(12) United States Patent
Yin et al.

(10) Patent No.: US 7,811,452 B2
(45) Date of Patent: Oct. 12, 2010

(54) MICROFLUIDIC DEVICE FOR SAMPLE ANALYSIS

(75) Inventors: Hongfeng Yin, Cupertino, CA (US); Reid Brennen, San Francisco, CA (US); Kevin Killeen, Woodside, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 399 days.

(21) Appl. No.: 12/022,684

(22) Filed: Jan. 30, 2008

(65) Prior Publication Data
US 2009/0188868 A1    Jul. 30, 2009

(51) Int. Cl.
*B01D 15/08* (2006.01)
(52) U.S. Cl. .................... 210/198.2; 210/656
(58) Field of Classification Search ................ 210/635, 210/656, 659, 143, 198.2, 502.1; 73/61.52, 73/61.56; 422/70, 101
See application file for complete search history.

(56) References Cited

U.S. PATENT DOCUMENTS

| | | | |
|---|---|---|---|
| 6,610,978 B2 | 8/2003 | Yin et al. | |
| 6,702,256 B2 | 3/2004 | Killeen et al. | |
| 6,845,968 B2 | 1/2005 | Killeen et al. | |
| 6,887,359 B2 * | 5/2005 | Ruggiero | 204/452 |
| 7,111,501 B2 | 9/2006 | Rocklin et al. | |
| 7,118,660 B2 | 10/2006 | Witt | |
| 7,128,876 B2 | 10/2006 | Yin et al. | |
| 7,138,062 B2 | 11/2006 | Yin et al. | |
| 7,214,320 B1 * | 5/2007 | Gregori et al. | 210/656 |
| 2003/0015682 A1 | 1/2003 | Killeen et al. | |
| 2003/0159993 A1 | 8/2003 | Yin et al. | |
| 2004/0156763 A1 | 8/2004 | Wood et al. | |
| 2004/0164265 A1 | 8/2004 | Killeen et al. | |
| 2005/0090013 A1 | 4/2005 | Myerson et al. | |
| 2006/0171855 A1 | 8/2006 | Yin et al. | |
| 2006/0186048 A1 * | 8/2006 | Tan | 210/656 |
| 2007/0071638 A1 * | 3/2007 | Kraiczek et al. | 422/57 |
| 2007/0140918 A1 | 6/2007 | Yin et al. | |

OTHER PUBLICATIONS

Yin et al., "Microfluidic Chip for Peptide Analysis with an Integrated HPLC Column, Sample Enrichment Column, and Nanoelectrospray Tip," Analytical Chemistry, vol. 77, No. 2, Jan. 15, 2005, pp. 527-533.
"DNA, RNA, Protein and Cell Analysis: Agilent 2100 bioanalyzer," Agilent Technologies, Product Brochure, 2007.

(Continued)

*Primary Examiner*—Ernest G Therkorn

(57) ABSTRACT

A device for sample analysis includes a microfluidic device for separating analytes of a sample comprising a liquid, the microfluidic device comprising a substrate having a first surface and a second surface opposite the first surface, the substrate defining features that collectively occupy an area of the substrate of about 0.1 to 10 cm$^2$, the features comprising a sample input port located at the first surface; a drying agent input port located at the first surface; an enrichment column; a separation column; switching ports located at the second surface; and fluid-conducting passages extending through the substrate from the switching ports to the sample input port, the drying agent input port, the enrichment column and the separation column. Also provided are methods and systems for separating analytes from a sample.

14 Claims, 9 Drawing Sheets

OTHER PUBLICATIONS

Holl et al., "Microfluidic Materials: Polymeric Laminate Technology," http://faculty.washington.edu/yagerp/microfluidicstutorial/polymericlaminates/polymericlaminates.htm Jul. 23, 2007.

Schilling, "Basic Microfluidic Concepts," http://faculty.washington.edu/yagerp/microfluidicstutorial/basicconcepts/basicconcepts.htm Jul. 23, 2007.

* cited by examiner

MICROFLUIDIC DEVICE FOR SAMPLE ANALYSIS

BACKGROUND

Microfluidic devices are used to control and manipulate very small volumes of fluids, often on the order of microliter or nanoliter volumes. Sometimes also referred to as a microfluidic device or a Lab-on-a-Chip, microfluidic devices are particularly useful in applications that employ rare or expensive fluids, such as proteomics and genomics. The small size of the microfluidic device allows for the analysis of minute quantities of a sample.

Some microfluidic devices are used for sample analysis by utilizing techniques such as chromatography to cause chromatographic separation of molecules within the sample. High-performance liquid chromatography (HPLC, sometimes also referred to as high-pressure liquid chromatography), involves pumping a liquid (the mobile phase) at high pressure through the separation column. Chromatographic separation occurs when the mobile phase carries molecules in the sample through the stationary phase where the molecules interact with the stationary phase surface. Different molecules interact differently with the stationary phase, resulting in the molecules having a different velocity through the separation column. This results in a separation of the molecules as they pass through the separation column. An enrichment column can also be used to enrich molecules in the sample before passing the sample through the separation column.

A difficulty can arise when a sample, such as a complex biological sample is dissolved in an organic solvent, because the organic solvent may not be compatible with the enrichment and/or separation column. In addition, the organic solvent can interfere and elute or partially elute the sample from the enrichment column and/or separation column before separation has occurred. Thus, there remains a need to develop methods and devices for resolution and separation of samples, such as complex biological samples.

DETAILED DESCRIPTION

Figure 1:
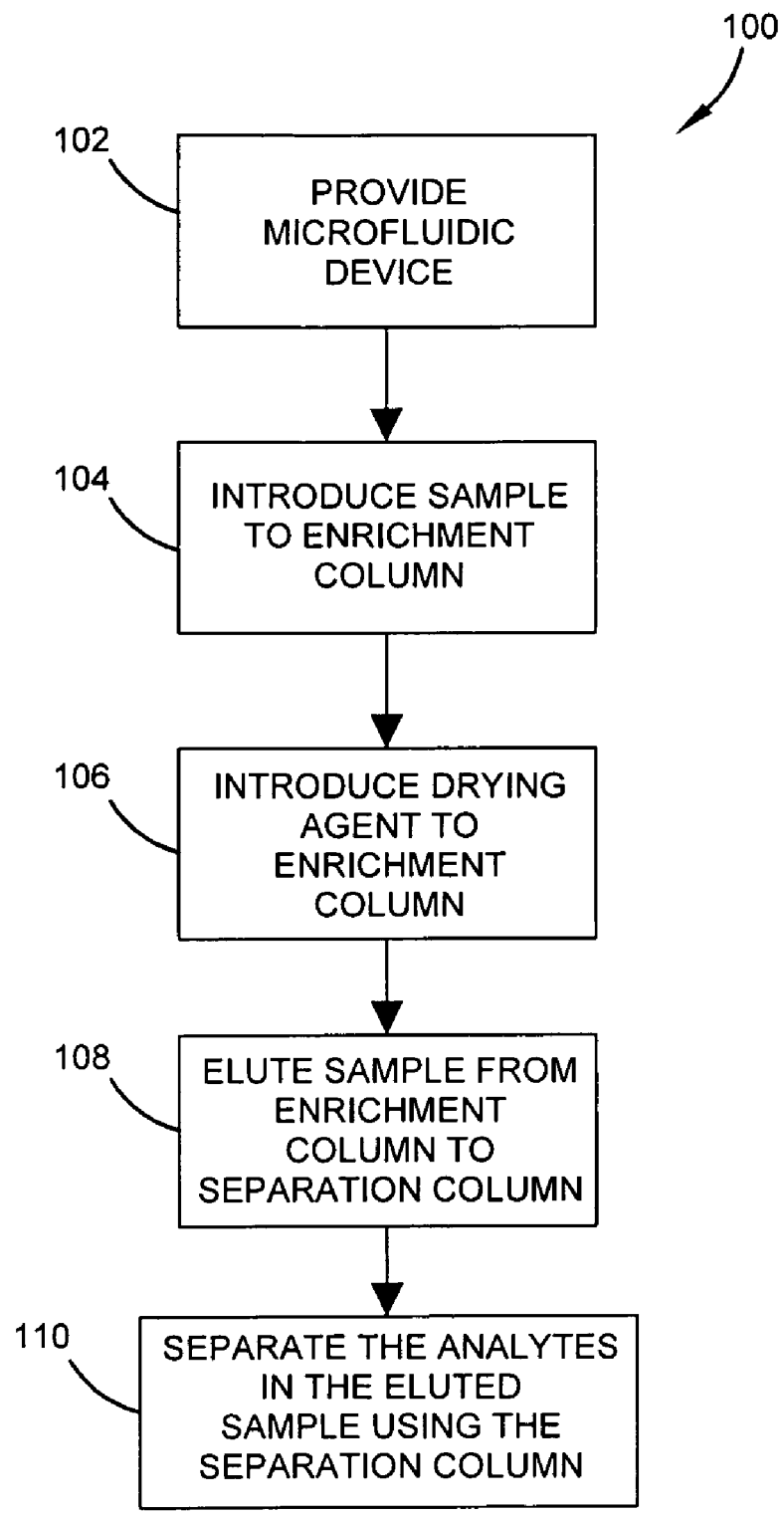
FIG. 1 is a flow chart illustrating an example of a method in accordance with an embodiment of the invention for separating analytes of a sample.

In general terms, this disclosure is directed to a microfluidic device for separating analytes of a sample comprising a liquid. In one possible configuration and by non-limiting example, the microfluidic device includes a substrate having a first surface and a second surface opposite the first surface. The substrate defines features that collectively occupy an area of the substrate of about 0.1 to 10 cm$^2$. The features include a sample input port, a drying agent input port, an enrichment column, a separation column, switching ports and fluid-conducting passages. The sample input port and the drying agent input port are located at the first surface of the substrate. The switching ports are located at the second surface of the substrate. The passages extend through the substrate from the switching ports to the sample input port, the drying agent input port, the enrichment column and the separation column. In an embodiment, the sample input port and the drying agent input port are located in a first region of the first surface of the substrate, at least some of the switching ports are located in a second region of the second surface of the substrate, and the first region is spatially offset from the second region in a direction parallel to the first surface. In an example, the first region is radially offset from the second region in the direction parallel to the first surface.

Various embodiments will be described in detail below with reference to the drawings, in which like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a flow chart showing an example a method 100 in accordance with an embodiment of the invention for separating analytes in a sample comprising a liquid. In the method, in block 102, a microfluidic device is provided. The microfluidic device includes a substrate that defines features that collectively occupy an area of the substrate ranging from about 0.1 cm$^2$ to about 10 cm$^2$. The features comprise an enrichment column and a separation column. In block 104, the sample is introduced into the enrichment column. In block 106, a drying agent is introduced into the enrichment column to remove liquid from the sample in the enrichment column. In block 108, the sample is eluted from the enrichment column to a separation column after liquid has been removed from the sample. In block 110, the analytes in the eluted sample are separated using the separation column.

Microfluidic devices are capable of processing small volumes of sample and of separating such analytes as are present in the present in the sample in a rapid and automated manner. Removing all or part of the liquid from the sample prior to separation avoids problems resulting from the presence of a liquid in the sample that can cause impaired separation.

Method 100 will now be described in greater detail with reference to FIG. 1. In block 102, a microfluidic device comprising an enrichment column and a separation column is provided. Examples of microfluidic devices and analysis systems that can be used to perform some embodiments of the method are described in detail below. In block 104, a sample is introduced into the enrichment column that constitutes part of the microfluidic device. The sample comprises a liquid and analytes. In some embodiments, the liquid is a solvent. In other embodiments, the sample is a suspension or a slurry including the liquid. The sample can be obtained from a variety of sources including, but not limited to, samples such as tissue, blood, hair, biopsy samples, urine, saliva, cells, plants, and water. Optionally, a sample is subject to one or more pre-processing operations to reduce the gamut of analytes present in the sample prior to introducing the sample into the enrichment column. In some embodiments, the analytes present in the sample are one or more of a protein, a peptide, a nucleic acid, an oligonucleotide, a drug or a drug metabolite. In some embodiments, the sample is contacted with a liquid that provides for isolation of one or more analytes from the sample. Non-limiting examples of such liquid include an organic solvent, a detergent, a buffer, a chaotropic salt, and combinations thereof. In some embodiments, the liquid in the sample is an organic solvent such as chloroform, ethanol, methanol, acetonitrile, and combinations thereof.

The sample can be introduced to the enrichment column using a variety of methods including injection through a port, or automated sample introduction. The enrichment column provides a material for binding of the analytes. The enrichment column includes, without limitation, normal phase, hydrophilic interaction phase, non-selective affinity phase, silica, cation and anion chromatography solid-phase material. Different embodiments of the enrichment column have different enrichment properties, e.g., enrichment properties for different target analytes. Additionally or alternatively, the sample can be introduced into more than one enrichment column with different enrichment properties. In an example, the sample flows through a first enrichment column having a first enrichment property and then flows through a second enrichment column having a second enrichment property. Additionally or alternatively, the enrichment column can be packed with mixed solid phases made by mixing ones of the materials noted above. As another example, the enrichment column can be packed such that adjacent sections are packed with different solid-phase materials.

In block 106, a drying agent is introduced into the enrichment column. The liquid of the sample introduced into the enrichment column is typically incompatible with a subsequent process, such as the separation process as described above. As a result, it is desirable to remove some or all of the liquid from the sample. The drying agent removes some or all of the liquid from the sample. Specifically, the drying agent passes through the enrichment column and partially or fully removes liquid from the sample. In embodiments, the drying agent is a gas, such as nitrogen or carbon dioxide. In other embodiments, the drying agent is a supercritical liquid, such as supercritical carbon dioxide. Other embodiments use other drying agents.

In block 108, after liquid has been removed from the sample, the analytes bound to the enrichment column from the sample are eluted from the enrichment column to the separation column that constitutes part of the microfluidic device. A mobile phase fluid is supplied to the enrichment column to transfer the analytes from the enrichment column to the separation column. In some embodiments, the mobile phase fluid is a solvent that elutes the analytes bound in the enrichment column from the enrichment column to the separation column. Examples of the mobile phase fluid are water, trifluoroacetic acid, buffer, salt, detergent, an organic solvent and combinations thereof. In some embodiments, the mobile phase fluid differs from the liquid in the sample in at least one of pH, organic content, aqueous content, and salt content. In some embodiments the mobile phase fluid comprises water, buffer, i.e., an aqueous solution comprising a salt, or a mixture of about 5% to 95% acetonitrile and 95% to 5% water.

In block 110, the analytes in the eluted sample is separated using the separation column. In some embodiments, the separation column is a liquid chromatography column. As the sample moves through the liquid chromatography column, the analytes of the sample are separated for subsequent analysis. The liquid chromatography column includes material for separating analytes. Examples of such materials include such standard LC materials as silica, reverse-phase silica, superficially-porous silica and the like. In some embodiments, separation of the analytes is achieved using a linear gradient or step gradient of a solvent flowed through the separation column.

In some embodiments, the method further includes analyzing the separated analytes. Analysis methods can include mass spectroscopy, nuclear magnetic resonance (NMR), absorbance, optical detection, and other methods known in the art. In embodiments in which mass spectroscopy is used, the separated analytes are ionized before analysis.

In some embodiments, the features defined in the substrate additionally comprise a sample input port configured to receive the sample, and a drying agent input port configured to receive the drying agent. The method additionally comprises providing a switching element in fluid communication with the substrate. The switching element comprises fluid transporting channels that provide selective fluid communication between the sample input port and the enrichment column, the drying agent input port and the enrichment column and the enrichment column and the separation column.

In some embodiments, the switching element comprises a rotor. In embodiments, the rotor comprises an inner rotor and an outer rotor concentric with the inner rotor. The outer rotor or the inner rotor selectively connects the sample input port or the drying agent input port to the enrichment column. In an embodiment, the substrate additionally comprises a waste port, and the inner rotor and the outer rotor each comprise respective fluid transporting channels.

When the sample is introduced to the enrichment column, the inner rotor is rotated to a first rotational state where its fluid transporting channels establish a first flow path extending to the waste port via the enrichment column, and the outer rotor is rotated to a first rotational state in which its fluid transporting channels establish a flow path extending from the sample input port to the first flow path established by the inner rotor. Additionally, in its first rotational state, the outer rotor inhibits flow of a drying agent through the drying agent input port. In this state, the rotors collectively establish a flow path through which the sample flows from the sample input port through the enrichment column and the sample liquid comprising non-bound material flows to the waste port.

When the drying agent is introduced into the enrichment column to remove liquid from the sample in the enrichment column, the outer rotor is rotated to a second rotational state in which its fluid transporting channels establish a flow path extending from the drying agent input port to the first flow path established by the inner rotor. In this state, the rotors provide a flow path through which the drying agent flows through the enrichment column. The rotors additionally establish a flow path extending from the sample input port to the waste port through which unneeded sample flows to waste.

When the sample is eluted from the enrichment column to the separation column after the drying agent has removed liquid from the sample, the inner rotor is rotated to a second rotational state in which its fluid transporting channels establish a flow path extending from the mobile phase fluid input port to the separation column via the enrichment column. In this state, the inner rotor provides a flow path through which the mobile phase fluid flows to the enrichment column and elutes the analytes bound therein, and through which the eluted analytes flows to the separation column. Additionally, the outer rotor is rotated to its first rotational state in which it inhibits the flow of the drying agent and allows unwanted sample (if any) to flow to waste.

Figure 2A:
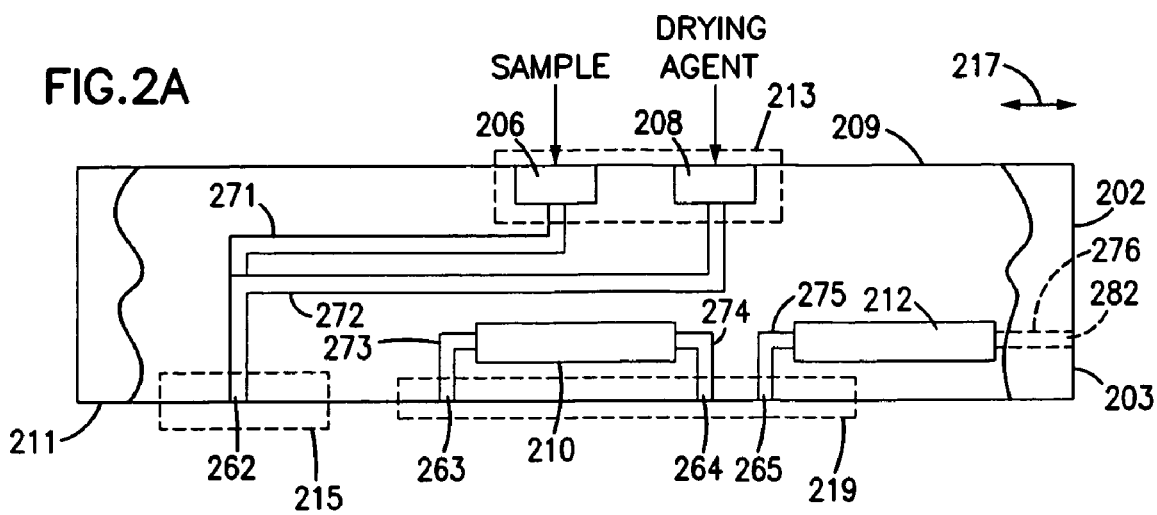
FIG. 2A is a cut-away side view showing an example of a microfluidic device in accordance with an embodiment of the invention.
Figure 2B:
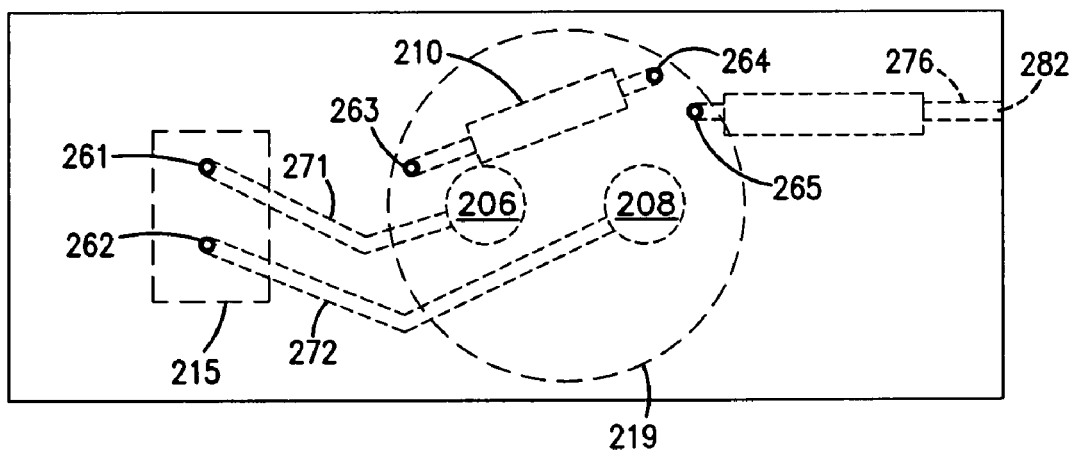
FIG. 2B is a plan view showing the microfluidic device shown in FIG. 2A.

FIG. 2A is a cut-away side view and FIG. 2B is a plan view showing an example of a microfluidic device 202 in accordance with an embodiment of the invention for separating components of a sample comprising a liquid. Microfluidic device 202 is for separating components of a sample comprising a liquid.

Microfluidic device 202 comprises a substrate 203. Substrate 203 is typically composed of one or more layers of materials such as, but not limited to, polymeric materials, ceramics (including aluminum oxide and the like), glass, metals, composites, and laminates thereof. Some suitable materials are described in more detail in U.S. Pat. No. 6,702,256 of Killeen et al., entitled *Flow-Switching Microdevice*, and incorporated by reference.

Substrate 203 has a first major surface 209 and a second major surface 211 opposite first surface 209. The major surfaces 209, 211 of substrate 203 are larger in area than the side and end surfaces of the substrate. Substrate 203 defines features that collectively occupy an area of the substrate ranging from about 0.1 cm$^2$ to about 10 cm$^2$. In the example shown in FIG. 2A, the features defined by the substrate are a sample input port 206, a drying agent input port 208, an enrichment column 210, a separation column 212, switching ports 261, 262, 263, 264 and 265 and fluid-conducting passages 271, 272, 273, 274, 275 and 276. More or fewer features may be defined in substrate 202. Sample input port 206 and drying agent input port 208 are located at the first surface 209 of substrate 203. In some embodiments, sample input port 206 and drying agent input port 208 are implemented as respective conduits that extend into substrate 208 from a major surface 209 thereof and through which a sample and a drying agent are received from a sample source (not shown) and a drying agent source (not shown) respectively. In the example shown, parts of passages 271-275 adjacent second surface 211 provide switching ports 261-265, respectively. Switching ports 261-265 are located to communicate fluidically with a switching element (not shown) when microfluidic device 202 interoperates with a host apparatus.

Passage 271 extends through substrate 203 from switching port 261 to sample input port 206. Passage 272 extends through substrate 203 from switching port 262 to drying agent input port 206. Passage 273 extends through substrate 203 from switching port 263 to one end of enrichment column 210. Passage 274 extends through substrate 203 from switching port 264 to the other end of enrichment column 210. Passage 275 extends through substrate 203 from switching port 265 to one end of separation column 212. Passage 276 extends through substrate 203 from the other end of separation column 212 to an output 282.

In the example shown, sample input port 206 and drying agent input port 208 are located at the first surface 209 of substrate 202 in a first region 213, and some of the switching ports 261-265, i.e., switching ports 261 and 262 connected to sample input port 206 and drying agent input port 208, respectively, are located at the second surface 211 of substrate 202 in a second region 215. Second region 215 is spatially offset from first region 213 in a direction 217 parallel to first surface 209. In the example shown, second region 215 is radially offset from first region 213. Remaining switching ports 263-265 are located at the second surface 211 of substrate 202 in a third region 219 substantially aligned with first region 213 in direction 217. The above-described arrangement of switching ports provides a host apparatus suitable for interoperation with microfluidic device 202 with the additional capability of interoperating with other microfluidic devices (not shown) that lack a drying agent input port.

Located in enrichment column 210 is a solid-phase material that binds to one or more analytes in the sample. The enrichment column includes, without limitation, normal phase, hydrophilic interaction phase, non-selective affinity phase, silica, cation and anion chromatography material. Different embodiments of microfluidic device 202 may comprise enrichment columns of different types with different enrichment properties. Additionally or alternatively, microfluidic device may comprise two or more enrichment columns. Such enrichment columns may be of the same type or of different types.

Separation column 212 is typically a liquid chromatography column. As the sample moves through the liquid chromatography column, the liquid chromatography column separates the analytes of the sample for subsequent analysis. Located in the liquid chromatography column is a solid-phase material for separating analytes. Examples of such solid-phase material are standard LC materials including silica, reverse phase silica, superficially porous silica or reverse phase silica and the like.

Figure 2C:
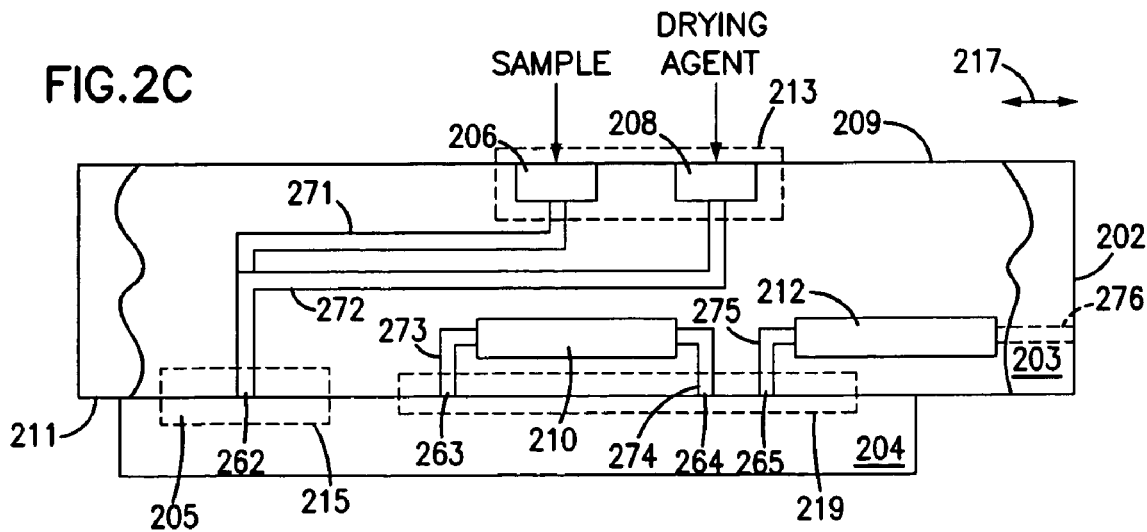
FIG. 2C is a side view showing an example of a system in accordance with an embodiment of the invention for separating components of a sample comprising a liquid.

FIG. 2C is a cut-away side view showing an example of a system 200 in accordance with an embodiment of the invention for separating components of a sample comprising a liquid. System 200 includes microfluidic device 202 and a switching element 204 in fluidic communication with microfluidic device 202. Switching device 204 constitutes part of a host apparatus that interoperates with microfluidic device 202. To simplify the drawing, the remainder of the host apparatus is not shown.

Switching element 204 is in fluid communication with microfluidic device 202, specifically with switching ports 261-265 defined in substrate 203. Switching element 204 includes fluid transporting channels that provide selective fluid communication via switching ports 261-265 between various ones of the passages 271-275 defined in the substrate 203 of microfluidic device 202, and, hence between the features to which the passages extend. Specifically, the fluid transporting channels of switching element 204 provide selective fluid communication between sample input port 206 and enrichment column 210, between drying agent input port 208 and enrichment column 210 and between the enrichment column and separation column 212. As such, switching element 204 controls the flow of the sample and the flow of the drying agent through the substrate. Thus, enrichment column 210 is in selective fluid communication with sample input port 206 and drying agent input port 208; and separation column 212 is in selective fluid communication with enrichment column 210.

In the example shown, switching element 204 is juxtaposed with the switching ports 261-265 defined in substrate 203 to establish fluid communication between microfluidic device 202 and switching element 204. This aligns the fluid transporting channels defined in switching element 204 with fluid-conducting channels 271-275 that extend through substrate 203 from switching ports 261-265 to sample input port 206, drying agent input port 208, enrichment column 210 and separation column 212, as described above.

In some embodiments, switching element 204 comprises a rotor. In some embodiments, the rotor comprises a first rotor and a second rotor concentric with the first rotor. In an embodiment in which the features defined in substrate 203 additionally include a waste port and a mobile phase fluid input port (not shown, but similar to mobile phase fluid input port 314 and waste port 316 described below with reference to FIG. 3) located in first region 213 and in which respective passages (not shown) extend from a switching port (not shown) located in third region 215 to the mobile-phase input port and from switching ports located in second region 213 and third region 215 to the waste port, the first rotor comprises fluid transporting channels and is selectively rotatable between a first rotational state and a second rotational state. In the first rotational state, the fluid transporting channels establish a first flow path extending to the waste port via enrichment column 210. In the second rotational state, the fluid transporting channels establish a second flow path extending from the mobile phase fluid input port to separation column 212.

In embodiments in which substrate 203 additionally defines a mobile phase fluid input port and a waste port (not shown) located in first region 213 and respective switching ports and passages as just described, the outer rotor comprises fluid transporting channels and is selectively rotatable between a first rotational state and a second rotational state. In the first rotational state, the fluid transporting channels establish a third flow path extending from sample input port 206 to the first flow path, and additionally inhibit flow of the drying agent through drying agent input port 208. In the second rotational state, the fluid transporting channels establish a fourth flow path extending from drying agent input port 208 to the first flow path, and establish a fifth flow path extending from sample input port 206 and the waste port. Embodiments of microfluidic device 202 will be described in detail below with reference to FIGS. 5-8.

Figure 3:
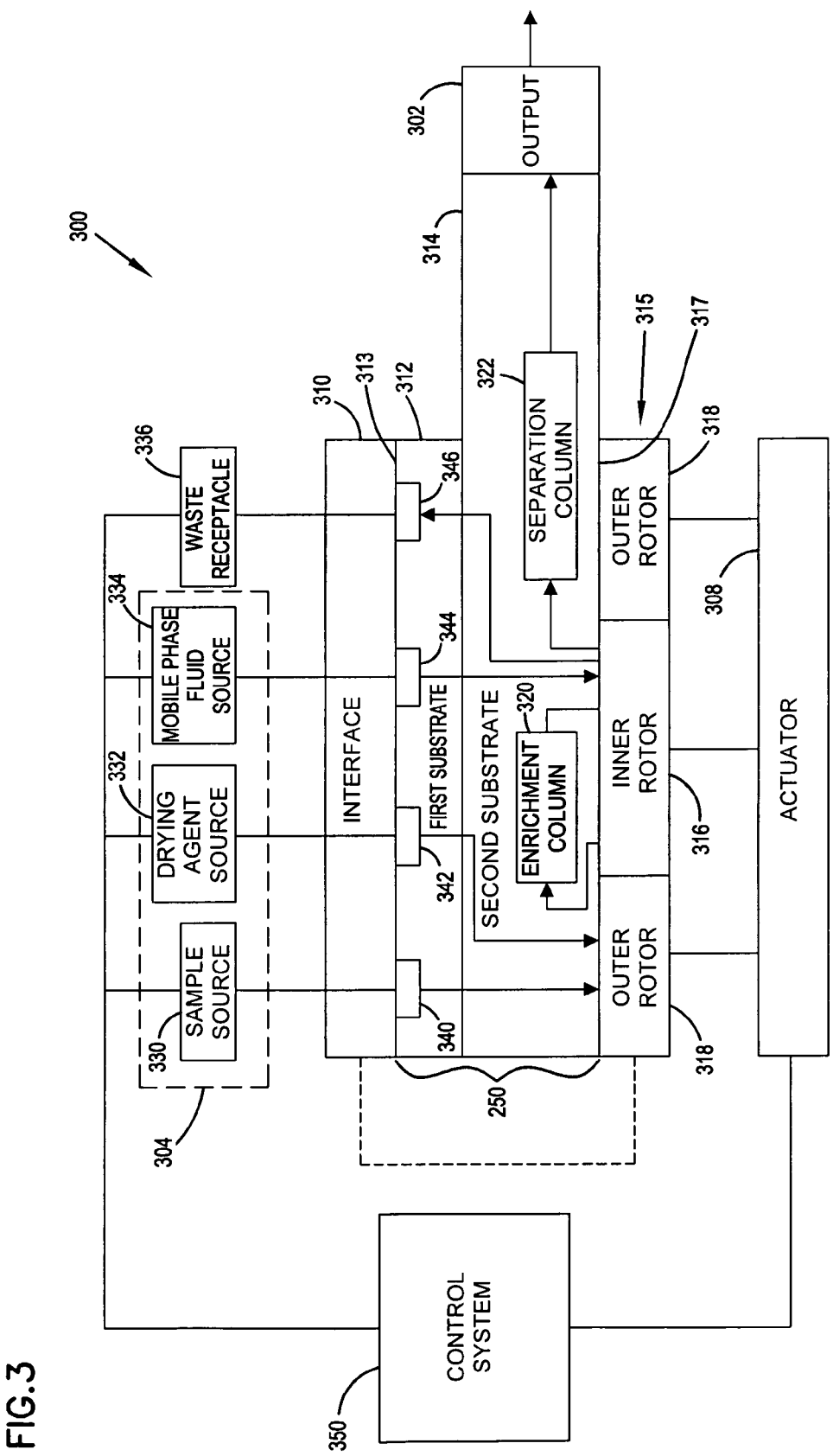
FIG. 3 is a block diagram showing an example of system in accordance with another embodiment of the invention for separating components of a sample comprising a liquid.

FIG. 3 is a block diagram showing an example of a system 300 in accordance with an embodiment of the invention for separating analytes of a sample comprising a liquid. System 300 is for separating analytes of a sample comprising a liquid, and includes another embodiment 250 of a microfluidic device in accordance with an embodiment of the invention. System 300 additionally includes sources 304, a waste receptacle 336, actuators 308, a microfluidic device interface 310 and switching element 315. At least microfluidic device interface 310 and switching element 315 constitute part of a host apparatus with which microfluidic device 250 interoperates. To simplify the drawing, the remainder of the host apparatus is not shown. Switching element 315 includes an inner rotor 316 and an outer rotor 318.

In system 300, microfluidic device 250 includes a substrate 303 composed of a first substrate layer 312 and a second substrate layer 314. First substrate layer 312 and a second substrate layer 314 collectively define features that collectively occupy a surface area of substrate 303 ranging from about 0.1 cm² to about 10 cm². First substrate layer 312 defines a sample input port 340, a drying agent input port 342, a mobile phase fluid input port 344 and a waste output port 346. Second substrate layer 314 defines an enrichment column 320 and a separation column 322 at least in part.

In the example shown, system 300 also includes a control system 350 that controls the operation of the system, and optionally links system 300 with other devices, such as with a mass spectrometer (not shown). Other examples lack a control system.

Sources 304, waste receptacle 336, actuators 308, interface 310, and, in some embodiments, control system 350 are typically parts of, or are connected to, the above-mentioned host apparatus (not shown) in which microfluidic device 250 is temporarily installed prior to analyzing a sample to form system 300. After use, microfluidic device 250 is typically discarded and a new microfluidic device is installed in the host apparatus ready to analyze the next sample. Device interface 310 is connected to sources 304 and waste receptacle 336 in the host apparatus. When microfluidic device 250 is installed in the host apparatus, device interface 310 is additionally in fluid communication with the first substrate layer 312 of microfluidic device 250. Device interface 310 includes input and output ports that are connected to sources 304 and waste receptacle 336 by fluid communication conduits, such as hoses, tubes, pipes, and the like. The fluid communication conduits direct the fluids from sources 304 to device interface 310 or from device interface 310 to waste receptacle 336. Device interface 310 includes flow paths aligned with corresponding ones of sample input port 340, drying agent input port 342, mobile phase fluid input port 344 and waste output port 346 of microfluidic device 250, and that direct the fluids received from sources 304 to the respective input ports, and that direct fluid received from waste output port 346 to waste receptacle 336.

In some embodiments, actuators 308 are mechanically coupled to device interface 310 within the host apparatus, such that device interface 310 also serves as a reference for rotation of rotors 316 and 318.

Sources 304 and waste receptacle 336 are illustrated as being connected with microfluidic device 250 through microfluidic device interface 310. In other embodiments, sources 304 and waste receptacle 336 are connected directly to microfluidic device 250. For example, sources 304 and waste receptacle 336 are connected in some embodiments to corresponding ones of sample input port 340, drying agent input port 342, mobile phase fluid input port 344 and waste output port 346 defined in the first substrate layer 312 of microfluidic device 250. Other embodiments have other connections.

The materials used to form the substrate layers 312 and 314 in embodiments of microfluidic device 250 described herein are selected with regard to physical and chemical characteristics that are desirable for proper functioning of the microfluidic device. In some embodiments, each substrate layer is fabricated from a material that is capable of microfabrication to define such features as conduits and channels, of micrometer or submicrometer dimensions. Microfabrication uses processes such as dry etching, wet etching, laser etching, laser ablation, molding, embossing, and the like. One or more layers of material can be deposited on the surface of a substrate layer, and features such as conduits and channels can be defined in such layers using one of the processes described above or another suitable process. For example, channels located on the surface of a glass substrate can be formed by depositing a layer of a photo-imageable polyimide on the surface of the glass substrate, and defining such channels in the polyimide layer. In some embodiments, the materials used to fabricate the microfluidic device are chemically inert and physically stable with respect to substances with which they come into contact, e.g., with respect to pH, electric fields, etc. Suitable materials for the microfluidic device include, but are not limited to, polymeric materials, ceramics (including aluminum oxide and the like), glass, metals, composites, and laminates thereof. Some suitable materials are described in more detail in the above-mentioned U.S. Pat. No. 6,702,256 of Killeen et al. Similar materials and fabrication processes can be used to fabricate device interface 310 and switching element 315.

In some embodiments, the microfluidic device has a single substrate. In other embodiments, such as the example shown in FIG. 3, the substrate is composed of a first substrate layer and a second substrate layer, as described above. When the microfluidic device is composed of a first substrate layer and a second substrate layer, the first and second substrate layers are in fluid-tight connection. In some embodiments, the first substrate layer and the second substrate layer are held together by pressure, for example, by using a clamp, a holder for each substrate, or by applying pressure using the switching element or the device interface or both. In other embodiments, the first substrate layer and the second substrate layer are attached to one another, for example, by an adhesive, lamination and the like.

Microfluidic device 250 can be fabricated using any convenient method, including, but not limited to, micromolding and casting techniques, embossing methods, surface micro-machining and bulk-micromachining. The latter technique involves formation of microstructures by etching directly into bulk material, typically using wet chemical etching or reactive ion etching (RIE). Surface micro-machining involves fabrication in films deposited on the surface of a substrate. In some embodiments, an exemplary surface micro-machining process known as Lithographie Galvanoformung Abformung (LIGA) is used to make a master that is then used in a stamping process to mass-produce microfluidic devices. See, for example, Becker et al., *Fabrication of Microstructures with High Aspect Ratios and Great Structural Heights by Synchrotron Radiation Lithography Galvanoforming, and Plastic Moulding (LIGA Process)*, MICROELECTRONIC ENGINEERING 4(1):35-36 (1986); Ehrfeld et al., 1988 *LIGA Process: Sensor Construction Techniques via X-Ray Lithography*, TECH. DIGEST FROM IEEE SOLID-STATE SENSOR AND ACTUATOR WORKSHOP, Hilton Head, S.C. (1988); Guckel et al., *Fabrication and Testing of the Planar Magnetic Micromotor*, J. MICROMECH. AND MICROENG. 1: 135-138 (1991). The fabrication technique used should define the features in substrate 303 with a definition commensurate with the dimensions of the features. Moreover, the fabrication technique should be capable of defining the features in first substrate layer 312 and second substrate layer 314 that constitute substrate 303 in a manner that allows precise alignment between the features defined in the respective substrate layers.

Returning to FIG. 3, microfluidic device 250 is sandwiched between device interface 310 and switching element 315. Specifically the major surface 313 of the first substrate layer 312 of microfluidic device 250 abuts the surface of the device interface remote from the connections to sources 304 and waste receptacle 336, and the major surface 317 of second substrate layer 314 abuts switching element 315.

First substrate layer 312 defines conduits and at least part of the channels that direct fluid received from sources 304 via device interface 310 within microfluidic device 250, and out to waste receptacle 336. Exemplary embodiments of first substrate layer 312 are described in more detail below. Second substrate layer 314 defines enrichment column 320 and separation column 322. In addition, second substrate layer 314 defines conduits and the remainder of the channels that direct fluid received from sources 304 within the microfluidic device 250, and out to waste receptacle 336. Exemplary embodiments of second substrate layer 314 are described in more detail below.

Although second substrate layer 314 is described as defining enrichment column 320, separation column 322, conduits and channels, other embodiments of second substrate layer 314 define only some of these features and may define additional features. Furthermore, features described above as defined in second substrate layer 314 can additionally or alternatively be defined in first substrate layer 312 or in additional substrate layers. Conversely, features described above as defined in first substrate layer 312 can additionally or alternatively be defined in second substrate layer 314 or in additional substrate layers. In other possible embodiments, one or more of the features described herein can be absent from microfluidic device 250.

In some embodiments, enrichment column 320 contains a normal phase packing material. In another embodiment, enrichment column 320 is a hydrophilic interaction chromatography (HILIC) enrichment column containing HILIC medium. Other embodiments include an ion-exchange chromatography column or a size exclusion chromatography column.

An example of separation column 322 is a liquid chromatography column, such as a reverse-phase liquid chromatography column. Separation column 322 contains a stationary phase. The stationary phase is a packing material, such as a normal-phase medium or a reverse-phase packing material. The stationary phase interacts with the sample to separate the sample. In other embodiments, separation column 322 is a high-performance liquid chromatography (HPLC) column.

In the example of system 300 shown in FIG. 3, switching element 315 is composed of inner rotor 316 and outer rotor 318 concentric with inner rotor 316. The concentric rotor arrangement shown enables a conventional substrate having a separation column defined therein to be used as second substrate layer 314 with only minor modifications. Rotors 316 and 318 include fluid transporting channels and each is rotatable independently of the other between a first rotational state and a second rotational state. In this way, rotors 316 and 318 operate together with channels defined in second substrate layer 314 to provide valves or flow-switching structures that control the flow of fluids received from sources 304 within microfluidic device 250. Rotors 316 and 318 are described in more detail below.

Although rotors 316 and 318 are described as concentric rotors, each having respective fluid transporting channels, other embodiments have additional rotors and different channel structures. Another embodiment has side-by-side rotors. A single rotor is another possible embodiment. Yet other embodiments do not include rotors, but rather include other valve or flow switching structures for controlling flow within microfluidic device 250.

As note above, first substrate layer 312, second substrate layer 314 form microfluidic device 250 that is removable from system 300. One of the benefits of device interface 310 is that it enables the microfluidic device to be removed from system 300 without requiring the disconnection of any of the fluid communication conduits extending from sources 304 and waste receptacle 306 to device interface 310. When microfluidic device 250 is installed in the host apparatus (not shown) to form system 300 as shown, pressure is applied between device interface 310 and switching element 315. Such pressure establishes a fluid-tight connection between device interface 310 and first substrate layer 312. In addition, the pressure applied between device interface 310 and switching element 315 establishes a fluid-tight connection between switching element 315 and second substrate layer 314. In some embodiments, pressure can be applied separately between device interface 310 and microfluidic device 250 and between switching element 315 and microfluidic device 250. The pressure is applied by a device, such as a clamp, spring, and the like, external to microfluidic device 250.

Microfluidic device 250 additionally has an output 302 for outputting the sample after chromatography has been completed. Some embodiments of output 302 include an electrospray nozzle (not shown) that ionizes the sample using an electric field, and passes the resulting ions to another device, such as ion optics or a mass spectrometer. Other embodiments include an output device other than an electrospray nozzle.

Each of the sources 304 provides a respective fluid to microfluidic device 250. Sources 304 include a sample source 330, a drying agent source 332, and a mobile phase fluid source 334. Sources 304 typically use pressure or gravity to advance the respective fluid through microfluidic device 250. The sample output by sample source 330 includes a liquid and includes analytes that microfluidic device 250 is configured to enrich and separate. In some embodiments, the liquid is an aqueous solvent or an organic solvent. In some embodiments, the sample is a solution comprising solid material, which includes the analytes, dissolved in an organic solvent, such as acetonitrile or methanol. In other embodiments, the solvent includes a combination of water and either acetonitrile or methanol. In yet other embodiments, sample source 330 provides a sample as a suspension or as a slurry.

As described above, it is desirable to remove liquid from the sample before inputting the sample into separation column 322. A drying agent provided by drying agent source 332 is used to remove some or all of the liquid from the sample provided by sample source 330. The analytes in the sample are then transferred to separation column 322. In some embodiments, drying agent source 332 provides a gas, such as nitrogen or carbon dioxide, as the drying agent. In other embodiments, drying agent source 332 provides a supercritical fluid, such as liquid carbon dioxide, as the drying agent. The drying agent provided by drying agent source 332 partially or fully removes the liquid from the sample provided by sample source 330.

Mobile phase fluid source 334 is used to provide to microfluidic device 250 a mobile phase fluid that transfers the analytes bound to or enriched by the enrichment column 320 to separation column 322. Mobile phase fluid source includes a source of pressure that advances the mobile phase fluid through flow paths defined in the microfluidic device 250. In some embodiments, mobile phase fluid source 334 comprises a nano pump that urges the mobile phase fluid through microfluidic device 250. In other embodiments, the pressure is provided by gravity. In possible embodiments, mobile phase fluid source 334 provides a small amount of a mobile phase liquid to microfluidic device 250 as the mobile phase fluid. The amount of mobile phase liquid provided is on the order of microliter or nanoliter volumes, for example. Other embodiments of mobile phase fluid source 334 provide other volumes of liquid or gas. In one embodiment, mobile phase fluid source 334 provides an aqueous solvent to microfluidic device 250. Other embodiments provide other fluids.

When microfluidic device 250 no longer has use for one or more of the respective fluids provided by sources 304, microfluidic device 250 directs the gas or fluid to waste receptacle 336. Waste receptacle 336 is connected to microfluidic device 250, such as by a tube, hose, pipe, or other fluid communication conduit, as described above. Waste receptacle 336 typically includes a bottle or other container for collecting waste. A pump is used in some embodiments to remove waste from microfluidic device 250. Additionally or alternatively, waste receptacle 306 is configured to recycle waste.

Actuators 308 are coupled between the host apparatus (not shown) and rotors 316 and 318. Actuators 308 operate electrically, hydraulically, pneumatically, manually, or in some other way to rotate rotors 316 and 318 relative to microfluidic device 250. In some embodiments, actuators 308 include one or more electric motors controlled by control system 350. Other embodiments include a separate actuator controller in communication with control system 350 or with another control system. In some embodiments, actuator 308 is implemented using two actuators, each connected to a respective one of rotors 316 and 318 to independently control the rotational states of the rotor relative to microfluidic device 250. In other possible embodiments, the rotors are manually actuated. A detent mechanism may be provided to define the rotation of each rotor in response to such manual actuation.

Figure 4:
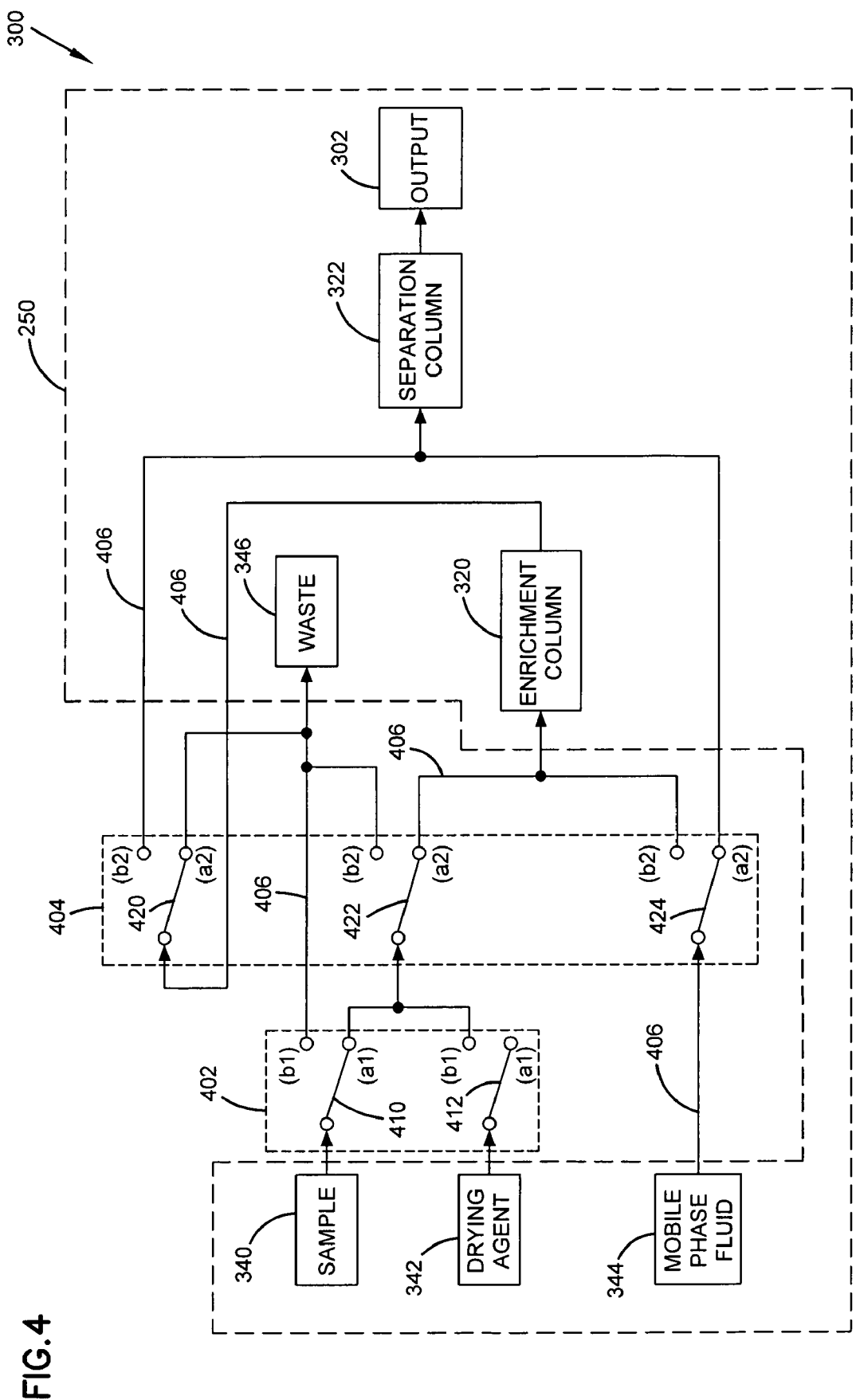
FIG. 4 is a schematic diagram showing the fluid flow switching performed in an exemplary embodiment of the system shown in FIG. 3.

FIG. 4 is schematic diagram showing an example of the fluid flow switching performed in an exemplary embodiment of system 300 shown in FIG. 3. Referring additionally to FIG. 3, system 300 receives sample, drying agent, and mobile phase fluid from sources 304, and passes waste to waste receptacle 336. System 300 includes first switching unit 402, second switching unit 404 and microfluidic device 250. The microfluidic device includes sample input port 340, drying agent input port 342, mobile phase fluid input port 344, waste output port 346, enrichment column 320, separation column 322, and flow paths 406. Flow paths 406 direct flow of the various fluids through microfluidic device 250.

First switching unit 402 includes flow switching devices 410 and 412. Second switching unit 404 includes flow switching devices 420, 422, and 424. The switching devices 410, 412 of first switching unit 402 switch simultaneously between a first position (a1) and a second position (b1). Additional positions are possible. Similarly, the switching devices 420, 422 and 424 of second switching unit 404 switch simultaneously between at least a first position (a2) and a second position (b2). Again, additional positions are possible. Examples of first switching unit 402 and second switching unit 404 are outer rotor 318 and inner rotor 316, respectively, shown in FIG. 3.

When first switching unit 402 is in the first position (a1), each switching device 410, 412 provides a flow path between the input of the switching device and the first position (a1) output of the switching device. When first switching unit 402 is in the second position (b1), each switching device provides a flow path between the input of the switching device and the second position (b1) output of the switching device. When second switching unit 404 is in the first position (a2), each switching device 420, 422, 424 provides a flow path between the input of the switching device and the first position (a2) output of the switching device. When second switching unit 404 is in the second position (b2), each switching device provides a flow path between the input of the switching device and the second position (b2) output of the switching device.

Some possible embodiments include only one switching unit, while other embodiments include two or more switching units. Other embodiments do not include switching units, but rather operate each switching device independently. In some embodiments, switching units 402 and 404 are controlled by control system 350 and actuators 308.

First switching unit 402 operates to select between the sample and the drying agent. When in the first position (a1), first switching unit 402 directs sample received at sample input port 340 to second switching unit 404 and inhibits the flow of the drying agent received at drying agent input port 342. The first position of first switching unit 402 is also referred to as a sample input mode. In the example shown, the flow of the drying agent is inhibited by connecting the second position of switching device 412 to a dead end, through which the drying agent cannot flow. Alternatively, the drying agent can be vented in the first position of first switching unit 402. When in the second position (b1), first switching unit 402 directs drying agent received at drying agent input port 342 to switching unit 404 and directs sample received at sample input port 340 to waste. The second position of first switching unit is also referred to as a drying agent input mode.

One of the flow paths 406 connects the a1 output of switching device 410 and the b1 output of switching device 412 in first switching unit 402 to the input of switching device 422 of second switching unit 404. Another of the flow paths connects the a2 output of switching device 422 to enrichment column 320. Another of the flow paths 406 connects the b1 output of switching device 410 to waste output port 346. Sample from sample source 330 comprises a liquid and analytes. Typically, the sample is in the form of a sample plug that constitutes part of a flow of a sample fluid provided by sample source 330. When the sample plug reaches switching units 402 and 404, first switching unit 402 is set to its first position and second switching unit 404 is set to its first position to cause the sample plug to flow to enrichment column 320. At other times, first switching unit 402 is set to its second position to cause the sample fluid coming before or after the sample plug to flow to waste output port 346. Examples of the sample fluid include a solvent or water. Other liquids can also be used.

Second switching unit 404 operates generally to select between a load mode, corresponding to the first position (a2), and a run mode, corresponding to the second position (b2). In the load mode, second switching unit 404 passes the sample or drying agent (depending on the position of first switching unit 402) through enrichment column 320 to waste output port 346. In the run mode, second switching unit 404 passes mobile phase fluid received at mobile phase fluid input port 344 to separation column 322 via enrichment column 320. The mobile phase fluid mobile phases sample remaining in enrichment column 320 after drying to separation column 322.

Flow paths 406 are any conduit capable of directing the flow of a gas or liquid within microfluidic device 250. In some embodiments, such conduits are provided by conduits or channels defined in or within one or more substrate layers, as described above. In some embodiments, flow paths 406 are microconduits having widths or diameters on the order of about 10 micrometers to about 200 micrometers, and having lengths on the order of about 10 micrometers to about 1 centimeter. These small sizes are beneficial, for example, in that they reduce the volumes of the fluids needed to perform an analysis of a sample using microfluidic device 250.

In some embodiments, switching units 402 and 404 are implemented using one or more rotors that include fluid transporting channels, as described above. The fluid transporting channels operate in cooperation with flow paths 406 defined in second substrate layer 314 as switching devices whose switching states depend on whether the rotor has been rotated to a first rotational state or a second rotational state. FIG. 3 shows an example in which switching units 402 and 404 are implemented using outer rotor 318 and inner rotor 316, respectively. Alternatively, switching units 402 and 404 may be implemented using inner rotor 316 and outer rotor 318, respectively. Non-concentric rotors are used in other embodiments. In further embodiments, valves or other fluid switching devices are used.

Figure 5:
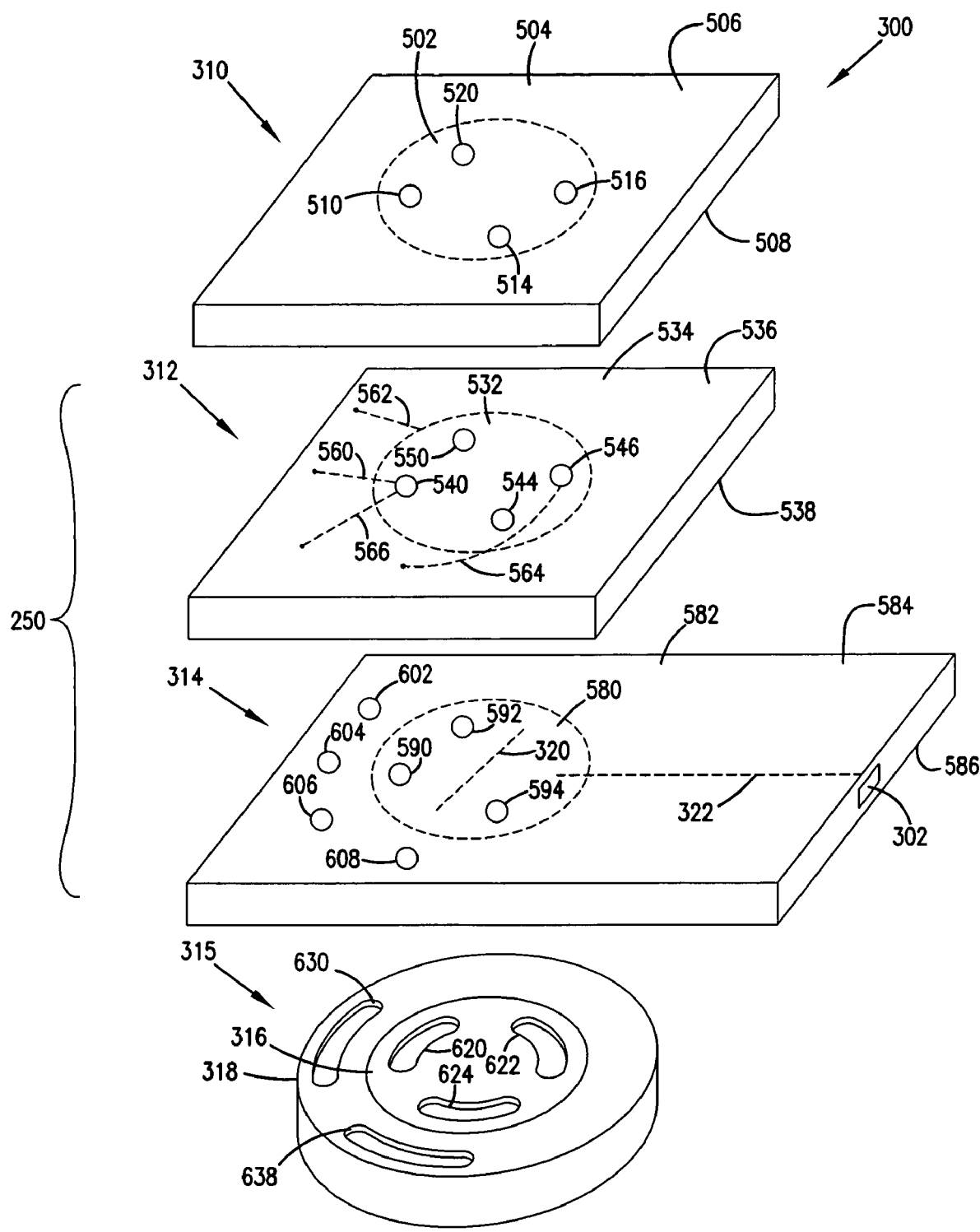
FIG. 5 is an exploded top perspective view showing part of the system shown in FIG. 3.
Figure 6:
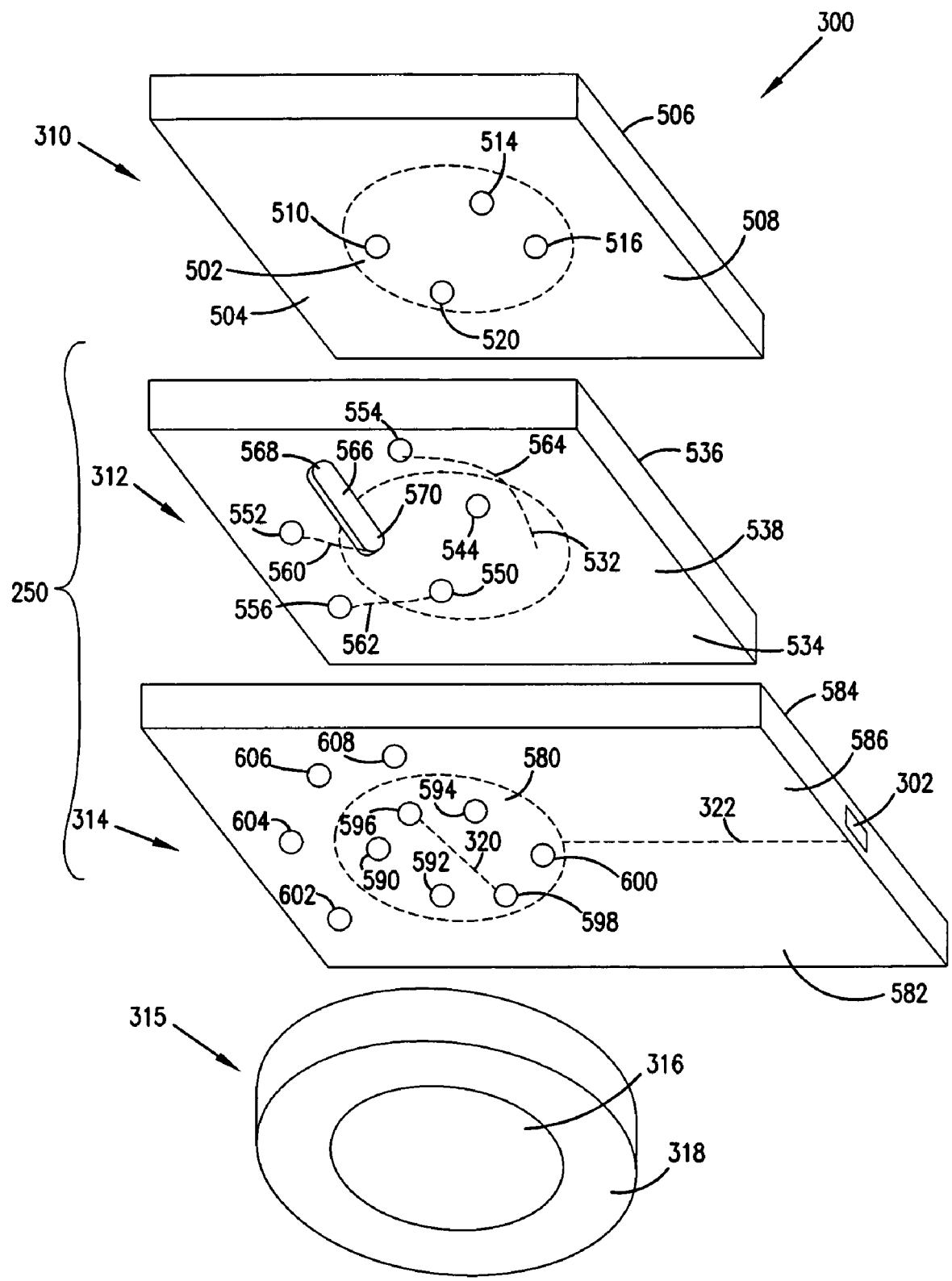
FIG. 6 is an exploded bottom perspective view showing part of the system shown in FIG. 3.

FIGS. 5 and 6 are exploded perspective views showing device interface 310, microfluidic device 250 and switching element 315 that constitute part of the example of system 300 described above with reference to FIG. 3. FIG. 5 is an exploded top perspective view. FIG. 6 is an exploded bottom perspective view. The example of microfluidic device 250 shown includes first substrate layer 312 and second substrate layer 314. As described above, second substrate 314 defines enrichment column 320 and separation column 322 in this embodiment.

Referring additionally to FIG. 3, fluids from sources 304 are received at device interface 310 and are directed through microfluidic device 250 by various flow paths. The flow paths are composed of conduits and channels defined in microfluidic device 250 and fluid transporting channels defined in switching element 315. The conduits and channels respectively extend substantially orthogonally and substantially parallel to the major surfaces of microfluidic device 205. Some of the flow paths include conduits that lead to inner and outer rotors 316 and 318 that operate in cooperation with the conduits to selectively direct the fluids through different ones of the flow paths, including those that lead to enrichment column 320 and separation column 322. By adjusting the rotational states of inner and outer rotors 316 and 318, microfluidic device 250 is controllable to perform the desired operations on the sample.

Referring to FIG. 5, device interface 310 has an inner region 502, an outer region 504, a surface 506, and a surface 508. Inner region 502 is aligned with inner rotor 316 and outer region 504 is aligned with outer rotor 318. In another possible embodiment, device interface 310 has inner region 502 only. Device interface 310 defines conduits that extend through inner region 502 and are fluidically coupled to receive respective fluids from, e.g., sample source 330, drying agent source 332, and mobile phase fluid source 334, and to expel waste to, e.g., waste receptacle 336. The conduits defined in device interface 310 include a conduit 510 coupled to sample source 330, a conduit 514 coupled to mobile phase fluid source 334, a conduit 516 coupled to drying agent source 332, and a conduit 520 coupled to waste receptacle 336. Additional conduits included in some embodiments provide additional inputs or outputs. At the locations of conduits 510, 514, 516 and 520, fluid communication conduits extend from the surface 506 of device interface 310 to sample source 330, mobile phase fluid source 332, drying agent source 334 and waste receptacle 336, respectively. Each fluid communication conduit is connected to surface 506 by such means as a pressure fitting or a fastener, such as one or more screws, adhesive, one or more clips, or other known fasteners. Conduits 510, 514, and 516 extend through device interface 310 from surface 506 to surface 508 and direct the flow of the respective fluid through device interface 310.

In microfluidic device 250, first substrate layer 312 includes an inner region 532, an outer region 534, a surface 536, and a surface 538 opposite surface 536. When microfluidic device 250 is installed in the host apparatus (not shown) of which device interface 310 and switching element 315 constitute part, inner region 532 is aligned with inner rotor 316 and the inner region 502 of device interface 310, and outer region 534 is aligned with outer rotor 318 and the outer region 504 of device interface 310. Conduits 540, 544, 546, and 550 are defined in the inner region 532 of first substrate layer 312 and provide the sample input port 340, the mobile phase fluid input port 344, the drying input port 342 and the waste output port 346, respectively, of microfluidic device 250. Conduits 544 and 550 extend through first substrate layer 312 from surface 536 to surface 538. Conduits 540 and 546 extend part-way through first substrate layer 312 from surface 536, but do not extend through to surface 538. When microfluidic device 250 is installed in the host apparatus, conduits 540, 544, 546 and 550 are in fluid communication with conduits 510, 514, 516 and 520, respectively, defined in device interface 310.

Referring to FIG. 6, conduits 552, 554, and 556 are defined in the outer region 534 of first substrate layer 312. Conduits 552, 554, and 556 extend part-way through first substrate layer 312 from surface 538, but do not extend through to surface 536.

Additionally defined in first substrate layer 312 are channels 560, 562, 564, and 566 that provide flow paths between inner region 532 and outer region 534. Channels 560, 562, and 564 are defined within first substrate layer 312. Channel 560 interconnects conduit 540 and conduit 552. Channel 562 interconnects conduit 550 and conduit 556. Channel 564 interconnects conduit 546 and conduit 554.

An open channel 566 extends into the first substrate layer 312 from surface 538. Channel 566 includes an end 568 and an end 570. When second substrate layer 314 is juxtaposed with first substrate layer 312, the surface 584 of second substrate layer 314 additionally bounds open channel 566 to form a closed channel. In this embodiment, the end 570 of channel 566 is aligned with conduit 540 that extends into first substrate layer 312 from surface 536. Conduit 540 provides sample input port 340 and is in fluid communication with conduit 510 defined in device interface 310. However, conduit 540 does not extend through first substrate layer 312 as far as channel 566. Rather, part of first substrate layer 312 separates channel 566 from conduit 540 so that there is no direct flow path from conduit 540 to channel 566.

Referring to FIG. 5, second substrate layer 314 includes an inner region 580, an outer region 582, a surface 584, and a surface 586 opposite surface 584. Enrichment column 320 is defined within the inner region 580 of second substrate layer 314. Separation column 322 is additionally defined within second substrate layer 314 and extends through a portion of inner region 580.

Referring to FIG. 5 and FIG. 6, conduits 590, 592, 594, 596, 598, and 600 are defined in the inner region 580 of second substrate layer 314. Conduits 590, 592, and 594 extend through second substrate layer 314 from surface 584 to surface 586. Conduits 596, 598, and 600 extend part-way through second substrate layer 314 from surface 586 but do not extend through to surface 584. Conduits 596 and 598 are located at the opposite ends of enrichment column 320. Conduit 600 is located at one end of separation column 322.

Conduit 590 is in fluid communication with the end 570 of channel 566 defined in first substrate layer 312. Conduit 592 is in fluid communication with conduit 550 defined in first substrate layer 312. Conduit 594 is in fluid communication with conduit 544 defined in first substrate layer 312. Conduit 600 is aligned with conduit 516 defined in device interface 310.

A portion of separation column 322 is defined within the outer region 582 of second substrate layer 314. Conduits 602, 604, 606, and 608 are additionally defined in outer region 582. Conduits 602, 604, 606, and 608 all extend through second substrate layer 314 from surface 584 to surface 586. Conduits 602, 604, 606, and 608 are respectively in fluid communication with conduit 556, conduit 552, the end 568 of channel 566, and conduit 554 all defined in first substrate layer 312.

As noted above, switching element 315 includes inner rotor 316 and outer rotor 318 concentric with inner rotor 316. Inner rotor 316 and outer rotor 318 are each one exemplary implementation of switching unit 404 and switching unit 402, respectively, described above with reference to FIG. 4. Rotors 316 and 318 are each rotatable independently of the other between a first rotational state and a second rotational state, as described in more detail below, to establish selective fluid communication among the various elements of microfluidic device 250. Inner rotor 316 includes fluid transporting channels 620, 622, and 624. Outer rotor 318 includes fluid transporting channels 630 and 638. Each rotor may include additional fluid transporting channels some of which may provide functions beyond the scope of this disclosure.

Outer rotor 318 is shown in its second rotational state in FIG. 5. In the second rotational state, outer rotor 318 establishes a flow path that directs the drying agent received at the drying agent input port provided by conduit 546 to inner rotor 316, and additionally establishes a flow path that directs the sample received at the sample input port provided by conduit 540 to the waste output port provided by conduit 550. In this second rotational state, fluid transporting channel 630 provides fluid communication between conduit 604 and conduit 602, and fluid transporting channel 638 provides fluid communication between conduit 606 and conduit 608. Conduits 602, 604 and 606, 608 are all defined in second substrate layer 314.

Outer rotor 318 also has a first rotational state, not shown in FIG. 5. In the first rotational state, outer rotor 318 establishes a flow path that directs the sample received at the sample input port provided by conduit 540 to inner rotor 316, and directs the drying agent received at the drying agent input port provided by conduit 546 to a dead end that inhibits the flow of the drying agent through microfluidic device 250. In this first rotational state, fluid transporting channel 630 provides fluid communication between conduit 604 and conduit 606, and fluid transporting channel 638 provides fluid communication between conduit 608 and a location on the surface 586 of second substrate layer 314 from which there is no outlet. Conduits 604, 606 and 608 are all defined in second substrate layer 314. Although the example of outer rotor 318 shown in FIG. 5 has two fluid transporting channels, other examples have more or fewer than two fluid transporting channels.

As noted above, inner rotor 316 also has two rotational states, and is shown in its second rotational state in FIG. 5. In the second rotational state, inner rotor 316 establishes a flow path that extends from mobile phase fluid port 514 through enrichment column 320 and through separation column 322 to output 302. In this second rotational state, fluid transporting channel 620 is aligned to connect conduit 590 with conduit 592, fluid transporting channel 622 is aligned to connect conduit 598 to conduit 600, and fluid transporting channel 624 is aligned to connect conduit 594 to conduit 596.

Inner rotor 316 also has a first rotational state, not shown in FIG. 5. In the first rotational state, inner rotor 316 establishes a flow path that directs sample or drying agent (depending on the rotational state of outer rotor 318) through enrichment column 320 and then to the waste output port provided by conduit 550, and additionally establishes a flow path that directs mobile phase fluid received at the mobile phase fluid input port provided by conduit 544 to separation column 322 and thence to output 302. In this first rotational state, fluid transporting channel 620 provides fluid communication between conduit 590 and conduit 596, fluid transporting channel 622 provides fluid communication between conduit 598 and conduit 592, and fluid transporting channel 624 provides fluid communication between conduit 594 and conduit 600. Conduits 590, 592, 594, 596, 598 and 600 are all defined in second substrate layer 314, Although some embodiments operate rotors 316 and 318 by rotating them in one direction (e.g., clockwise) into one rotational state, and then rotating them in the other direction (e.g., counter-clockwise) into the other rotational state, this is not required in all embodiments. Other embodiments operate one or both of rotors 316 and 318 in other ways. For example, in embodiments in which the rotors are rotationally symmetrical, the rotors can be rotated in only one direction (e.g., clockwise), to achieve the same flow switching function.

Figure 7:
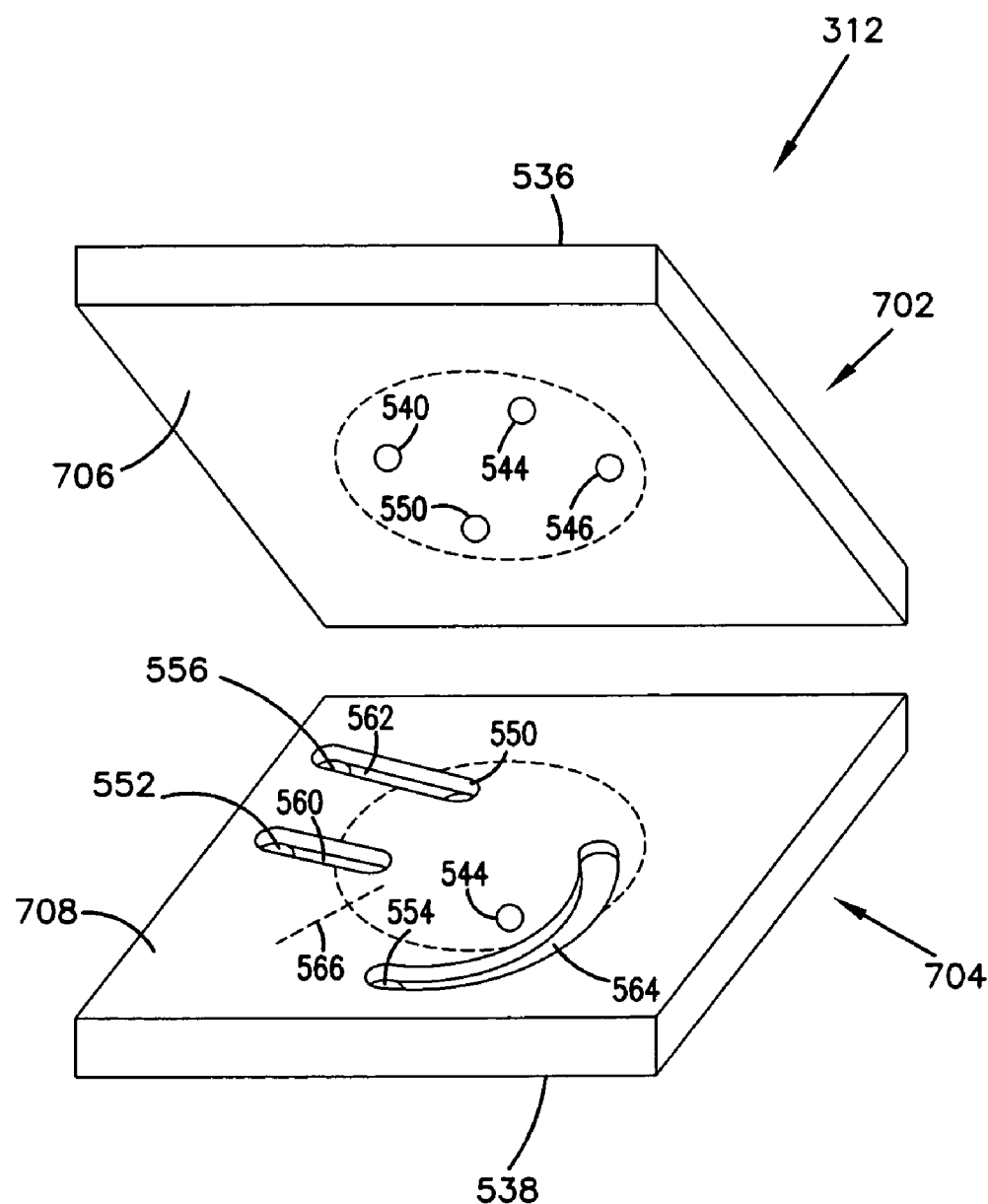
FIG. 7 is an exploded perspective view showing an example of the first substrate of the microfluidic device shown in FIG. 3.

FIG. 7 is an exploded perspective view showing an example of the first substrate layer 312 of microfluidic device 250 described above with reference to FIG. 3. In the example shown, first substrate layer 312 is composed of a first sub-layer 702 and a second sub-layer 704. First sub-layer 702 has surface 536 as an exterior surface and an interior surface 706 opposite surface 536. Second layer 704 has an interior surface 708 and surface 538 opposite surface 708 as an exterior surface. Surfaces 536 and 538 are the same as the surfaces 536 and 538 of first substrate layer 312 shown in FIGS. 5 and 6. First and second sub-layers 702 and 704 are connected at interior surfaces 706 and 708, such as by an adhesive or some other type of fastening, to form first substrate layer 312. In other embodiments, first and second sub-layers 702 and 704 are held together by pressure, such as by pressure applied between device interface 310 and switching element 315 (shown in FIG. 3), or pressure applied in some other way.

First sub-layer 702 defines conduits 540, 544, 546, and 550 that extend from exterior surface 536 to interior surface 706. Second sub-layer 704 defines conduits 544, 550, 552, 554, and 556 that extend from interior surface 708 to exterior surface 538. Second sub-layer 704 also defines channels 560, 562, and 564 that extend part-way into second sub-layer 704 from interior surface 708, and channel 566 (shown in FIG. 6) that extends part-way into second sub-layer 704 from exterior surface 538. The above-described conduits and channels are formed in sub-layers 702, 704 by any desired method, such as ablating, cutting, grinding, etching, and the like. In another possible embodiment, one or more of the channels 560, 562, and 564 are defined in first sub-layer 702 and extend part-way into the first sub-layer from interior surface 706, or in are defined in both first sub-layer 702 and second sub-layer 704 extending part-way into the respective sub-layers from the respective interior surfaces 706, 708 thereof.

Other possible embodiments of first substrate layer 312 are composed of more than two sub-layers. For example, first substrate layer 312 can be composed of three sub-layers. In such an embodiment, channels 560, 562, and 564 are defined in a third sub-layer (not shown) located between first sub-layer 702 and second sub-layer 704. Channels 560, 562 and 564 extend through the entire thickness of the third sub-layer. Other embodiments have more than three layers.

Figure 8:
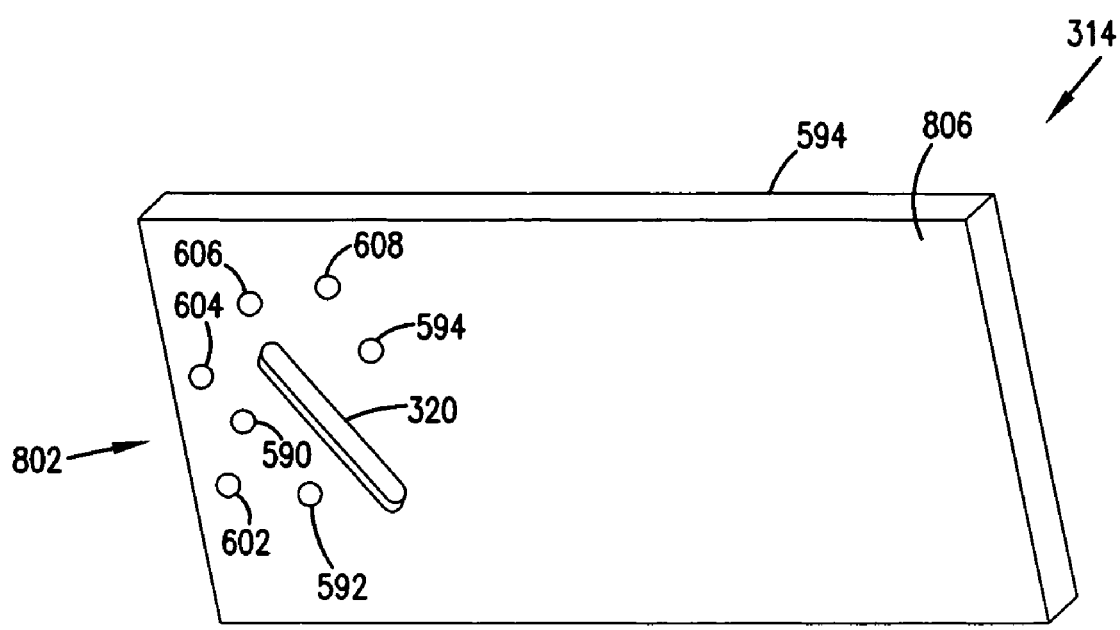
FIG. 8 is an exploded perspective view showing an example of the second substrate of the microfluidic device shown in FIG. 3.
Figure 8:
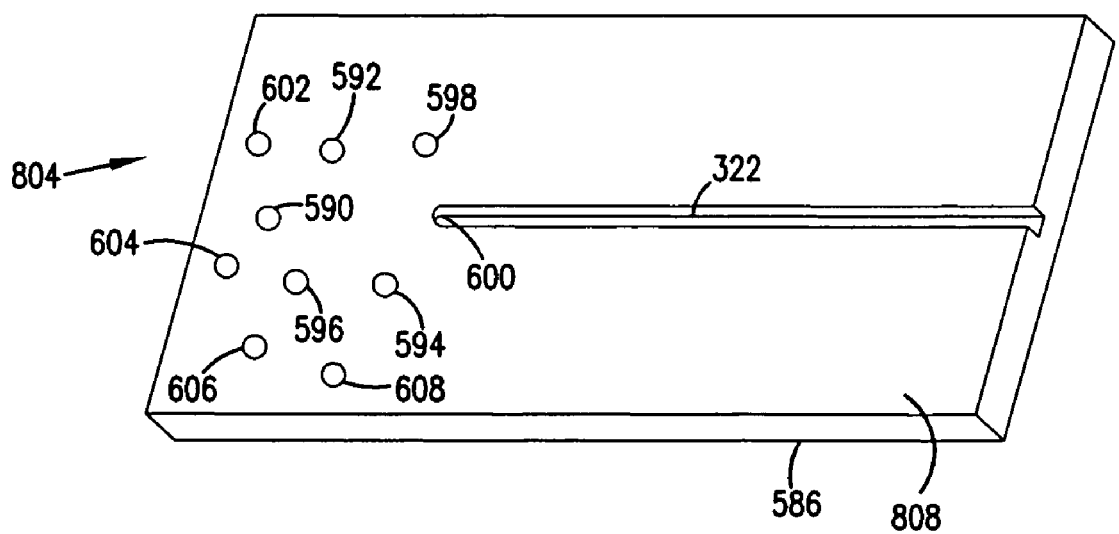

FIG. 8 is an exploded perspective view showing an example of the second substrate layer 314 of microfluidic device 250 described above with reference to FIG. 3. In the example shown, second substrate layer 314 is composed of a first sub-layer 802 and a second sub-layer 804. First sub-layer 802 has surface 584 as an exterior surface, and an interior surface 806 opposite surface 584. Second layer 804 has an interior surface 808 and surface 586 opposite surface 808 as an exterior surface. Surfaces 584 and 586 are the same as the surfaces 584 and 586 of second substrate layer 314 shown in FIGS. 5 and 6. First and second sub-layers 806 and 808 are connected at interior surfaces 806 and 808, such as by an adhesive or some other type of fastening, to form second substrate layer 314. In other embodiments, first and second layers 802 and 804 are held together by pressure, such as by pressure applied between device interface 310 and switching elements 315 (shown in FIG. 3), or by pressure applied in some other way.

First sub-layer 802 defines conduits 590, 592, 594, 602, 604, 606, and 608 that extend from surface 584 to interior surface 806. First sub-layer 802 also defines enrichment column 320 that extends part-way into first sub-layer 802 from interior surface 808. Second sub-layer 804 defines conduits 590, 592, 594, 596, 598, 600, 602, 604, 606, and 608 that extend from interior surface 808 to exterior surface 586. Second sub-layer 804 also defines separation column 322 that extends part-way into second sub-layer 804 from interior surface 808. The above-described conduits and channels are formed in the sub-layers by any desired method, such ablating, cutting, grinding, etching, and the like. In another possible embodiment, second sub-layer 804 defines enrichment column 320 and first sub-layer 802 defines separation column 322. In another embodiment, first sub-layer 802 or second sub-layer defines both enrichment column 320 and separation column 322. In another embodiment, enrichment column 320 and separation column 322 extend part-way into both sub-layers 802 and 804.

Other possible embodiments of second substrate layer 314 are composed of more than two sub-layers. For example, second substrate layer 314 can be composed of three sub-layers. In such an embodiment, separation column 320, enrichment column 322 and part of each of the above-mentioned conduits are defined in a third sub-layer located between first sub-layer 802 and second sub-layer 804. Other embodiments have more than three layers.

Figure 9:
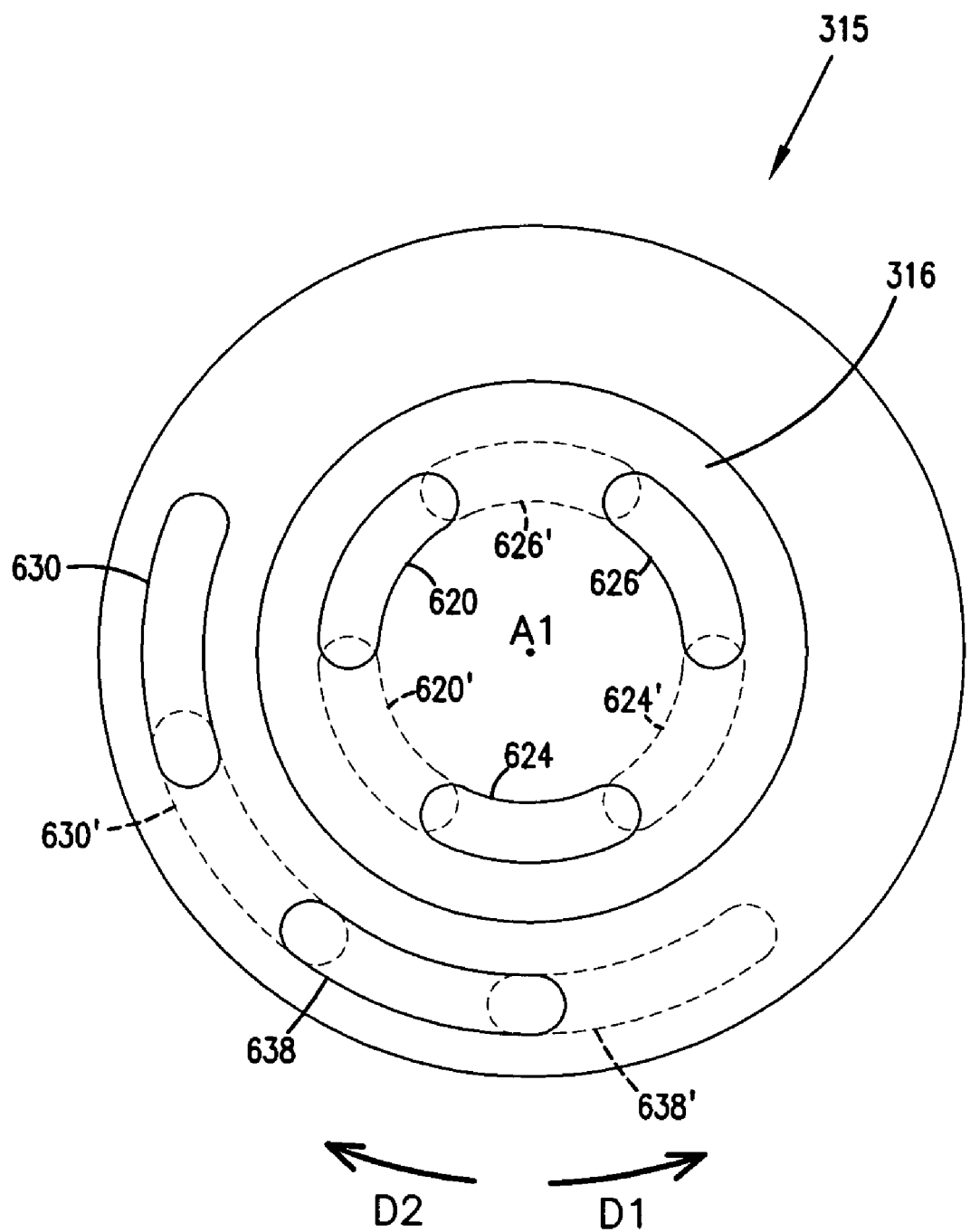
FIG. 9 is a top view showing an example of the switching element of the system shown in FIG. 3.

FIG. 9 is a top view showing an example of the switching element 315 of system 300 described above with reference to FIG. 3. Switching element 315 is composed of inner rotor 316 and outer rotor 318. Inner rotor 316 defines fluid transporting channels 620, 624, and 626. Outer rotor 318 defines fluid transporting channels 630 and 638. Inner and outer rotors 316 and 318 are each rotatable independently of the other between a first rotational state and a second rotational state. The positions of the fluid transporting channels when the rotors are in their first rotational states are indicated using broken lines. Reference numerals 620', 624', 626', 630', and 638' indicate the locations of fluid transporting channels 620, 624, 626, 630, and 638, respectively, when the rotors are in their first rotational states. To rotate each of the rotors 316 and 318 to its second rotational state, the respective rotor is rotated in direction D2 until the fluid transporting channels of the rotor are positioned as illustrated using solid lines. This rotational state corresponds to that shown in FIG. 5, relative to microfluidic device 250. To return each of the rotors 316 and 318 to its first rotational state, the respective rotor is rotated in direction D1 until the fluid transporting channels of the rotor are positioned as illustrated by the broken lines. As noted above, in rotationally-symmetrical examples of the rotors, the rotors can be returned to a functional equivalent of the first rotational state by rotating the rotor in direction D2. In the example shown, inner rotor 316 is rotationally symmetrical, but outer rotor 318 is not. Outer rotor 318 could be made rotationally symmetrical by defining two more pairs of fluid transporting channels at 120-degree intervals in outer rotor 318. Each pair of fluid transporting channels is similar to fluid transporting channels 630 and 638.

The various embodiments described above are provided by way of illustration and should not be construed to limit the claims attached hereto.

We claim:

1. A system for separating analytes of a sample comprising a liquid, the system comprising:
   a microfluidic device comprising a substrate defining features that collectively occupy an area of the substrate of about 0.1 to 10 cm$^2$, the features comprising:
   a sample input port configured to receive the sample;
   a drying agent input port configured to receive a drying agent;
   an enrichment column in selective fluid communication with the sample input port and the drying agent input port; and
   a separation column in selective fluid communication with the enrichment column; and
   a switching element in fluid communication with the microfluidic device, the switching element comprising fluid transporting channels that provide the selective fluid communication between the sample input port and the enrichment column, the drying agent input port and the enrichment column and the enrichment column and the separation column.

2. The system of claim 1, in which the substrate comprises:
a first substrate layer defining the sample input port and the drying agent input port; and
a second substrate layer defining at least part of the enrichment column and the separation column.

3. The system of claim 1, wherein the enrichment column comprises a hydrophilic interaction chromatography enrichment column.

4. The system of claim 1, wherein the separation column is a reverse phase liquid separation column.

5. The system of claim 1, wherein the switching element comprises a rotor.

6. The system of claim 5, wherein:
the rotor comprises an inner rotor and an outer rotor concentric with the inner rotor; and
one of the inner rotor and the outer rotor selectively connects the drying agent input port to the enrichment column.

7. The system of claim 6, wherein:
the features defined in the substrate additionally comprise a mobile phase fluid input port and a waste output port; and
one of the rotors comprises fluid transporting channels and is selectively rotatable between a first rotational state and the second rotational state;
the fluid transporting channels in the first rotational state establish a first flow path extending to the waste port via the enrichment column; and
the fluid transporting channels in the second rotational state establish a second flow path extending from the mobile phase fluid input port to the separation column via the enrichment column.

8. The system of claim 7, wherein:
the other of the rotors comprises fluid transporting channels and is selectively rotatable between a first rotational state and a second rotational state;
the fluid transporting channels in the first rotational state establish a third flow path extending from the sample input port to the first flow path and additionally inhibit flow of a drying agent through the drying agent input port; and
the fluid transporting channels in the second rotational state establish a fourth flow path extending from the drying agent input port to the first flow path and establish a fifth flow path extending from the sample input port to the waste port.

9. A microfluidic device for separating analytes of a sample comprising a liquid, the microfluidic device comprising a substrate having a first surface and a second surface opposite the first surface, the substrate defining features that collectively occupy an area of the substrate of about 0.1 to 10 cm$^2$, the features comprising:
a sample input port located at the first surface;
a drying agent input port located at the first surface;
an enrichment column;
a separation column;
switching ports located at the second surface; and
fluid-conducting passages extending through the substrate from the switching ports to the sample input port, the drying agent input port, the enrichment column and the separation column.

10. The microfluidic device of claim 9, wherein:
the sample input port and the drying agent input port are located at the first surface in a first region;
ones of the switching ports are located at the second surface in a second region; and
the first region is spatially offset from the second region in a direction parallel to the first surface.

11. The microfluidic device of claim 10, wherein the first region is radially offset from the second region in the direction parallel to the first surface.

12. The microfluidic device of claim 10, wherein:
others of the switching ports are located at the second surface in a third region; and
the third region of the second surface is substantially aligned with the first region of the first surface in the direction parallel to the first surface.

13. The microfluidic device of claim 9, wherein:
the substrate comprises a first substrate layer and a second substrate layer, the second substrate layer in fluid-tight contact with the first substrate layer;
the first substrate layer defines the sample input port and the drying agent input port;
the second substrate layer defines at least part of the enrichment column.

14. The microfluidic device of claim 9, wherein the features defined in the substrate additionally comprise:
a mobile phase fluid input port;
a waste output port; and
additional fluid-conducting passages extending from the switching ports to the mobile phase fluid input port and the waste output port.

* * * * *